United States Patent [19]
Shaw

[11] Patent Number: 5,261,818
[45] Date of Patent: Nov. 16, 1993

[54] MULTI-FLUTED DENTAL IRRIGATION DRILL

[76] Inventor: Leon Shaw, 1225 Broken Sound Pkwy., NW., Boca Raton, Fla. 33487

[21] Appl. No.: 912,167

[22] Filed: Jul. 13, 1992

[51] Int. Cl.⁵ .......................... A61C 3/02; A61C 3/06
[52] U.S. Cl. ...................................... 433/165; 433/166
[58] Field of Search ................................ 433/165, 166

[56] References Cited

U.S. PATENT DOCUMENTS

| | | | |
|---|---|---|---|
| 4,021,920 | 5/1977 | Kirschner et al. | 433/165 X |
| 4,820,156 | 4/1989 | Ross | 433/165 |
| 5,085,586 | 2/1992 | Johnson | 433/224 |
| 5,098,293 | 3/1992 | Lööf et al. | 433/165 |

FOREIGN PATENT DOCUMENTS 447423  8/1927  Fed. Rep. of Germany ...... 433/165

Primary Examiner—Cary E. O'Connor
Assistant Examiner—Cindy A. Cherichetti
Attorney, Agent, or Firm—M. K. Silverman

[57] ABSTRACT

A dental drill exhibits the form of a substantially solid cylindrical body having a cutting portion and a gripping shank. The cylindrical body includes a boss between the cutting portion and said gripping shank. Upon the cutting portion, between the boss and a tip of the cutting portion, are provided at least four axi-symmetric flutes upon a lateral surface of the cutting portion. Each of the flutes are substantially co-axial with the longitudinal axis of the drill, defining a substantially linear profile before reaching the conical tip of the cutting portion, at which each of the flutes narrows. The flutes are separated by substantially co-axial channels having radial depths of about one-eighth of the diameter of the cylindrical body. Each of the channels flare to a larger polar dimension at said tip of the cutting portion. The body is provided with an axial irrigation channel having at least one liquid outlet within each of the channels and proximally to the tip of the cutting portion of the drill. The improved drill affords superior control to the dentist and decrease trauma to the patient.

16 Claims, 1 Drawing Sheet

MULTI-FLUTED DENTAL IRRIGATION DRILL

BACKGROUND OF THE INVENTION

The present invention relates to dental drills (also known as bits) and, more particularly, to so-called fluted irrigation spade drills employed in the creation of channels in the human jawbone prior to the insertion of an implant or post upon which a dental structure such as a bridge is to be placed.

The difficulty in the usage of prior art dental drills of the above type is that, due to rotational eccentricity and flutter relative to the axis of rotation of the drill, a degree of trauma is imparted to the jawbone of the dental patient. Also, the dentist cannot effectively control pressure and depth of penetration of the drill where eccentricity or flutter exists in the drill action.

It is known in the prior art to employ two flutes in the cylindrical axi-symmetric structure of irrigation drills. It has however been determined as a result of usage over a period of years that the use of two flutes in a drill gives rise to an undesirable level of eccentricity. Efforts to solve this problem by the addition of a third flute have not produced a substantially better result.

The instant invention suggests the use of four or more axi-symmetric flutes and, in addition, the use of axially separated circumferential score marks or serrations to provide to the dentist a greater control over depth of penetration. The instant invention is therefore concerned with the provision of a superior cutting tool to the dental practitioner, that is concerned with the implant area of dental implants, to enable such practitioners to accomplish a maximum of osiointegration of the implant within the implant site of the jawbone.

SUMMARY OF THE INVENTION

The inventive dental drill exhibits the form of a substantially solid cylindrical body having a cutting portion and a gripping shank. The cylindrical body includes a boss between the cutting portion and said gripping shank. Upon the cutting portion proper, between said boss and a tip of the cutting portion, are provided at least four axi-symmetric flutes upon a lateral surface of the cutting portion. Each of said flutes are substantially co-axial with the longitudinal axis of the drill, thereby, defining a substantially linear profile before reaching said conical tip of the cutting portion, at which each of the flutes narrows. The flutes are separated by substantially co-axial channels having radial depths of about one-eighth of the diameter of the cylindrical body. Each of said channels flare to a larger polar dimension at said tip of the cutting portion. Said body is provided with axial irrigation channel having at least one liquid outlet within each of said channels and proximally said tip of the cutting portion of the drill.

It is accordingly an object of the present invention to provide an improved irrigation drill having particular utility in creating precise depth and diameter of bores in jawbones at sites of dental implant insertion.

It is another object of the invention to provide a drill of the above type that will minimize eccentricity and flutter in the rotation thereof, thusly minimizing trauma to the jaw of the patient.

It is a further object of the present invention to provide an irrigation dental spade drill that will enable improved control of pressure and depth of penetration by the dentist.

It is a yet further object of the invention to provide a dental drill of the above type which will afford improved accuracy in the cutting action thereof.

The above and yet other objects and advantages of the present invention will become apparent form the hereinafter set forth Brief Description of the Drawings, Detailed Description of the Invention and Claims appended herewith.

DETAILED DESCRIPTION OF THE INVENTION

Figure 1:
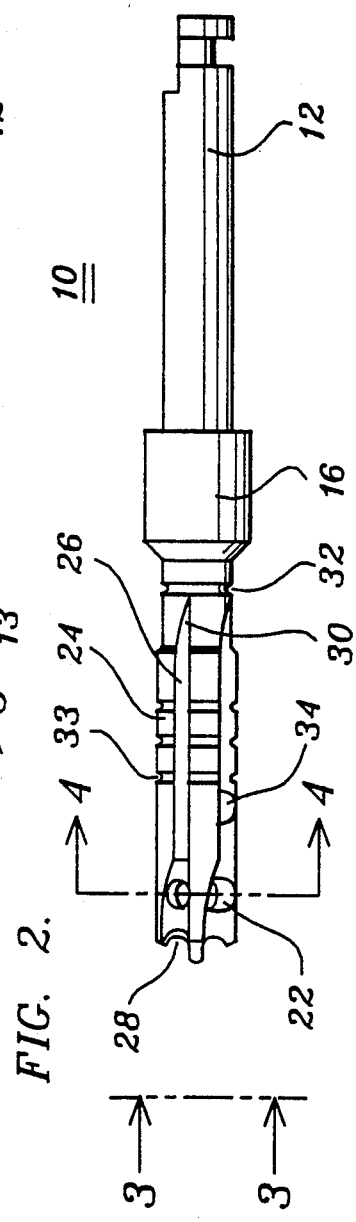
FIG. 1 is an axial elevational view of the inventive dental drill.
Figure 2:
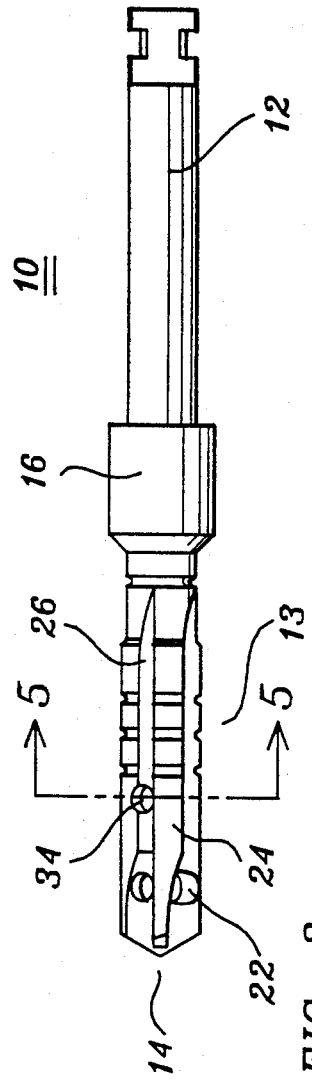
FIG. 2 is an axial elevational view of the drill axially rotated ninety degrees from the view of FIG. 1.
Figure 6:
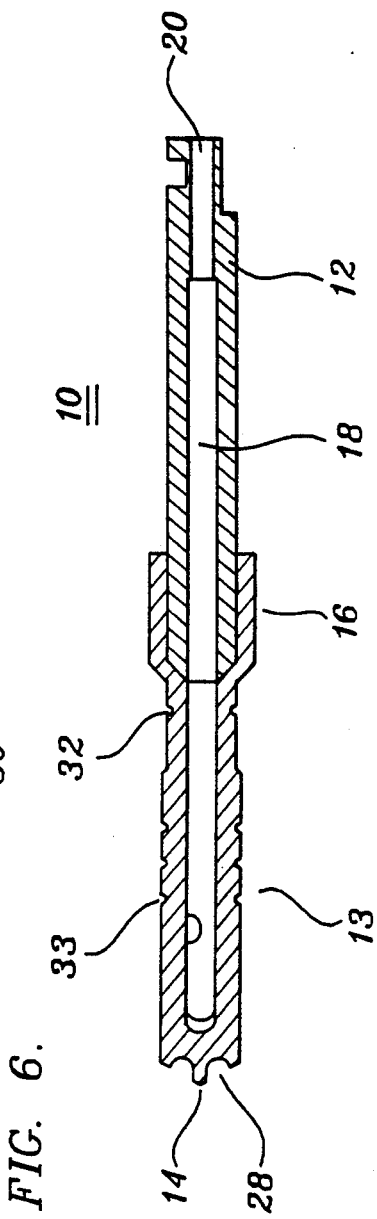
FIG. 6 is an axial cross-sectional view of FIG. 2.

With reference to the views of FIGS. 1, 2, and 6, the inventive irrigation spade drill may be seen to comprise a substantially solid cylindrical body 10 having a gripping shank 12 and cutting portion 13 having a working tip 14 which is in the general form of a cone when seen in the orientation of FIG. 1. Located somewhat in the middle of cylindrical body 10 at the end of shank 12 is an annular boss 16. Running the entire axial length of the drill is an irrigation channel 18 having input 20 and a plurality of outlets 22 proximal to said working tip 14. As may be particularly noted in the views of FIGS. 1 and 3, there are, formed within the lateral surface of the cylindrical body 10, at least four flutes 24 that are disposed axi-symmetrically about irrigation channel 18. It is noted that each flute 24 defines a peripheral profile that is substantially co-axial with said irrigation channel 18. Each flute 24 is separated from its neighboring flute by substantially co-axial channels 26 that extend from said boss 16 to the area of said irrigation channel outlets 22 at which each flute narrows somewhat. As noted in FIGS. 1 and 2, each channel 26 flares to a larger polar dimension at lower end 28, and tends to fishtail away from the axis of the irrigation channel at the opposite end 30 thereof.

It is to be appreciated that the pitch of the lines of interface, between flutes 24 and bores 26, which exist particularly at opposite ends thereof may be manufactured in either a clockwise or counterclockwise manner to produce either left-hand or right-hand cutting capabilities, as may be desired by the individual practitioner.

It has been determined that through the use of four or more such axi-symmetric flutes 24, eccentricity, that is, wiggle and flutter of the drill during use, is markedly reduced, while control by the dentist is improved.

Figure 4:
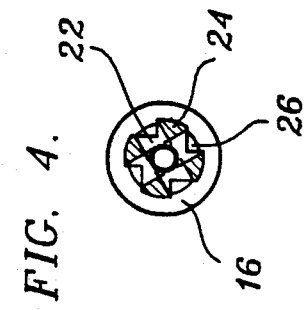
FIG. 4 is a radial cross-sectional view taken along Line 4—4 of FIG. 2.
Figure 3:
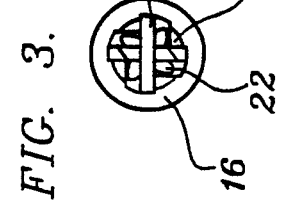
FIG. 3 is a left plan view of the drill taken along Line 3—3 of FIG. 2.
Figure 5:
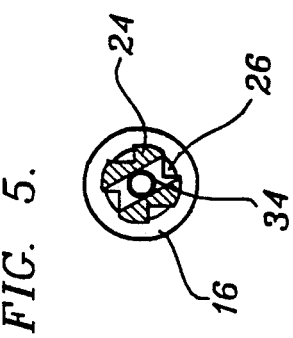
FIG. 5 is a radial cross-sectional view taken along Line 5—5 of FIG. 1.

The pecular radial cross-sectional and tip geometry of the drill may be seen with reference to the views of FIGS. 3, 4 and 5. More particularly, in FIG. 4 is shown the location of irrigation channel outlets 22 in each channel 26. In FIG. 5 is shown the location of irrigation outlets 34 in alternating channels.

As a further advantageous feature of the instant invention there are provided a plurality of serrations 32 the first of which 33 begins at eight millimeters from tip 14 followed, at separations of two millimeters, with four successive serrations. The serrations are circumferential grooves extending about the lateral surface of the cutting portion 13 between outlets 34 and boss 16. Through the use of such serrations, the depth of penetration of the drill can be readily controlled by the dental practitioner.

In a preferred embodiment, the radial depth of each channel 26 will be between one-tenth and one-quarter of the overall diameter of the drill which is typically 2 to 7 millimeters. The entire length of drill is typically about 20 to 25 millimeters.

In the preferred embodiment there are four flutes 24.

It is noted that shank 12 is manufactured as a discrete element from cutting portion 13 in which, upon assembly, a fluid-tight seal is employed to define a permanent complemental contact between the shank and cutting portion.

Accordingly, while there has been shown and described the preferred embodiment of the instant invention it may be appreciated that the invention may be embodied otherwise than is herein specifically shown and described and that within said embodiment, certain changes may be made within the form and arrangement of the parts without departing from the underlying ideas or principles of this invention within the scope of the Claims appended herewith.

Having thus described my invention what I claim as new, useful and non-obvious and, accordingly, secure by Letters Patent of the United States is:

1. A dental drill in the form of a substantially solid cylindrical body having a gripping shank, the drill comprising:
    (a) an annular boss located between said cutting portion and said gripping shank; and
    (b) a cutting portion including at least four axi-symmetric flutes formed upon a lateral surface thereof, each of said flutes defining substantially co-axial peripheral profiles, each of said flutes separated by substantially co-axial channels, said cylindrical body having an irrigation channel extending the entire length thereof and having at least one outlet within each of said channels, said one outlet of each channel located proximally to a substantially conical tip of said cutting portion, said tip comprising a surface formed integrally and continuously with ends of said flutes and channels located remotely from said annular boss.

2. The dental drill as recited in claim 1 in which said at least four flutes comprises exactly four flutes.

3. The dental drill as recited in claim 1 in which said co-axial channels between said flutes define a radial depth of between one-tenth and one-quarter of the diameter of the cutting portion of the cylindrical body.

4. The dental drill as recited in claim 3, in which the diameter of said cylindrical body is about 2 to about 7 millimeters.

5. The dental drill as recited in claim 3 in which, proximally to said tip of said cutting portion the polar dimension of said channels increases as the polar dimension of said flutes decreases.

6. The dental drill as recited in claim 5, in which said irrigation channel possesses alternately two outlets and one outlet at polarly successive co-axial channels.

7. The dental drill as recited in claim 5, in which said cutting portion of said cylindrical body, between said conical tip and said boss, includes a plurality of equally axially displaced serrations, whereby sensing of depth of cutting penetration can be assisted thereby.

8. The dental drill as recited in claim 7, in which said serrations begin at a distance of about eight millimeters from said tip and continue at intervals of about two millimeters until reaching said annular boss.

9. The dental drill as recited in claim 5 in which said shank comprises an element manufactured apart from said cutting portion in which a fluid-tight seal defines a permanent press-fit complemental contact therebetween.

10. The dental drill as recited in claim 1, in which said irrigation channel possesses alternately two outlets and one outlet at polarly successive channels.

11. The dental drill as recited in claim 1, in which said cutting portion of said cylindrical body, between said conical tip and said boss, includes a plurality of equally axially displaced serrations, whereby sensing of depth of cutting penetration is assisted thereby.

12. The dental drill as recited in claim 11 in which said serrations begin at a distance of about eight millimeters from said tip and continue at intervals of about two millimeters until reaching said annular boss.

13. The dental drill as recited in claim 12 in which the total length of said solid cylindrical body is about 20 to 25 millimeters.

14. The dental drill as recited in claim 12 in which said co-axial channels between said flutes define a radial depth of between one-tenth and one-quarter of the diameter of the cutting portion of the cylindrical body.

15. The dental drill as recited in claim 14, in which the diameter of said cylindrical body is about 2 to about 7 millimeters.

16. The dental drill as recited in claim 14, in which said irrigation channel possesses alternately two outlets and one outlet at polarly successive co-axial channels.

* * * * *